(12) United States Patent
Garrison

(10) Patent No.: US 6,241,521 B1
(45) Date of Patent: Jun. 5, 2001

(54) BITE BLOCK

(76) Inventor: John E. Garrison, 110 De Witt La., Spring Lake, MI (US) 49456

( * ) Notice: Subject to any disclaimer, the term of this patent is extended or adjusted under 35 U.S.C. 154(b) by 0 days.

(21) Appl. No.: 09/304,200

(22) Filed: May 3, 1999

Related U.S. Application Data

(63) Continuation of application No. PCT/US98/14476, filed on Jul. 13, 1998.

(51) Int. Cl.$^7$ .................................................. A61C 17/06
(52) U.S. Cl. .............................................................. 433/140
(58) Field of Search ..................... 433/93, 140; 600/238, 600/239, 243, 244

(56) References Cited

U.S. PATENT DOCUMENTS

| | | |
|---|---|---|
| D. 297,665 | 9/1988 | Neeley . |
| 886,522 * | 5/1908 | Kyle .................................. 600/244 |
| 903,344 * | 11/1908 | Wackler ............................ 433/140 |
| 1,143,515 | 6/1915 | Dunlop . |
| 1,229,595 * | 6/1917 | De Brul ............................. 433/140 |
| 2,220,674 | 11/1940 | Bloomheart . |
| 2,651,109 * | 9/1953 | Kanter ............................... 433/140 |
| 2,823,455 | 2/1958 | Sprague . |
| 3,722,101 | 3/1973 | Via, Jr. . |
| 4,356,821 | 11/1982 | Rind . |
| 4,887,965 * | 12/1989 | Fox .................................... 433/140 |
| 4,944,313 | 7/1990 | Katz et al. . |
| 4,975,057 * | 12/1990 | Dyfvermark ........................ 433/93 |
| 5,009,595 | 4/1991 | Osborn . |
| 5,152,300 * | 10/1992 | Horst ................................... 433/93 |
| 5,421,327 | 6/1995 | Flynn et al. . |
| 5,466,153 | 11/1995 | Poindexter . |
| 5,590,643 | 1/1997 | Flam . |

FOREIGN PATENT DOCUMENTS

180607 * 6/1922 (GB) ................................. 600/238

* cited by examiner

Primary Examiner—Ralph A. Lewis
(74) Attorney, Agent, or Firm—Rader, Fishman, Grauer & McGarry, An Office of Rader, Fishman & Grauer PLLC

(57) ABSTRACT

A bite block for facilitating a dentist's access to a patient's mouth includes an open-ended, U-shaped body having a pair of arms extending from a bight portion, thereby defining a void 40 that is bounded in part by the arms and the bite portion, whereby when the bite block is positioned between upper and lower teeth of the patient's mouth the dentist will have access to the patient's mouth through the void.

18 Claims, 2 Drawing Sheets

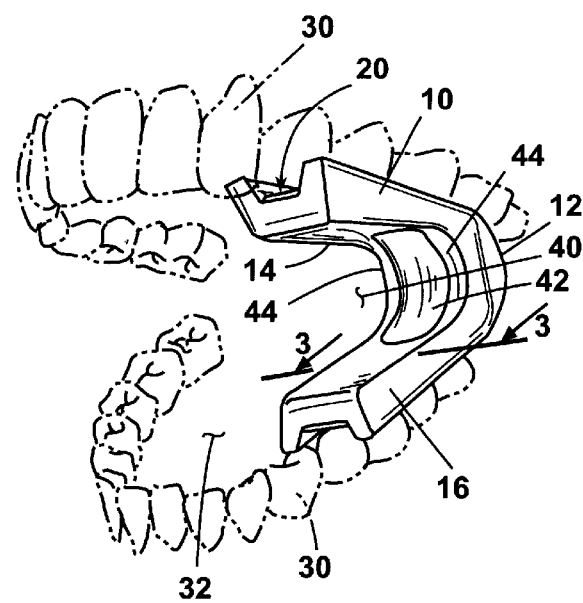
Fig. 1
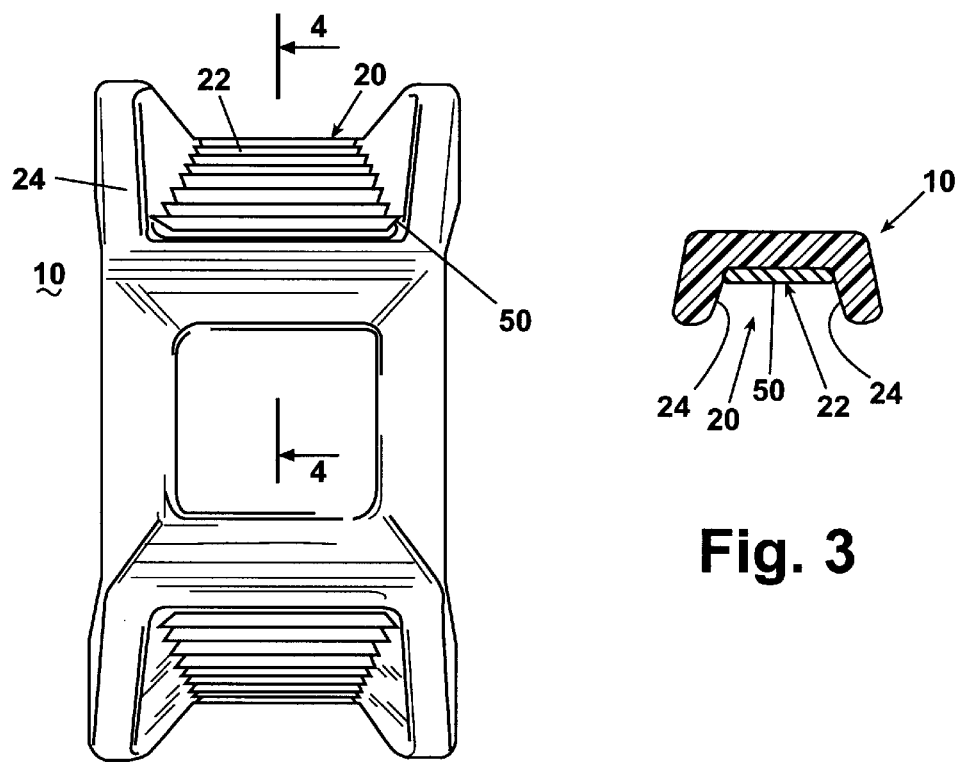
Fig. 2
Fig. 3

BITE BLOCK

CROSS-REFERENCE TO RELATED APPLICATION

This application is a continuation of PCT Application Ser. No. PCT/US98/14476 filed on Jul. 13, 1998.

BACKGROUND OF THE INVENTION

1. Field of the Invention

This invention relates to dentistry apparatus and, more particularly, it relates to mouth props for dental patients.

2. Description of the Related Art

Dental mouth props, or bite blocks, are devices which are inserted into the patient's mouth between the upper and lower teeth to keep the mouth opened in a fixed position while the dentist is working therein. In typical use, the teeth on one side of the mouth contact the bite block while the dentist is working on teeth on the opposite side. These bite blocks enhance the efficiency of the dentist so that the dentist does not have to continually remind the patient to keep the mouth open at a certain angle, and further so that the dentist does not have to be concerned with the patient inadvertently biting the dentist's hands. Patients typically find the props useful, as they are able to relax the muscles in the jaw as they rest their teeth on the prop.

Bite blocks are even more useful during long dental appointments when the patient's jaw muscles fatigue. The bite block allows the patient to relax the muscles and teeth on the block, which does the work in keeping the mouth open. Also, some patients cannot open their mouths to provide the dentist access because of damage to the jaw joint. These patients in particular require bite blocks even for short appointments.

Many different designs of bite blocks have been used or are otherwise known. However, known bite blocks are generally inconvenient to use and uncomfortable. Current designs are made of elastic material molded around a stiff metal frame, which allow for little to no variability in the opening angle. Such designs put stress on the mouths of patients who cannot open as wide as others. Current designs also deny access to assistants who evacuate oral fluids and tooth debris while the dentist prepares the tooth. Some examples of prior art bite blocks are shown in U.S. Pat. No. 3,722,101 issued to Via, Jr.; U.S. Pat. No. 500,959 issued to Osborn; and U.S. Pat. No. 5,421,327 issued to Flynn et al. The Via patent discloses a disposable, polygonal-shaped bite block made from a non-elastic foam material such as polyurethane, whereby the force of the teeth on the block causes the teeth to indent into the material and lock the block in place. The Via prop, however, consumes too much mouth space, and therefore competes with the space in which the dentist works. The Via prop is also invariable in size, which proves to be uncomfortable to some patients.

The Osborn patent describes a bite block formed of a pliable styrene material. While the Osborn patent improves access to the patient's mouth by providing a window in the block through which the dentist can insert tools, the block is somewhat complicated in construction and includes flanges extending from the top and bottom of the block on the cheek side to stabilize and keep the soft tissue of the cheeks away from the working area. This design still consumes too much work area despite the included window.

The bite blocks in both of the aforementioned patents are rigid in construction. The lack of flexibility in size of the bite block or adjustability of the particular patient's mouth causes strain to the mouth when the dentist is accessing the patient's mouth. Moreover, the aforementioned props block access to the patient's mouth from at least one direction. The Osborn device provides a window for extending tools therethrough but this window is still comparably small and therefore limits the dentist's access to the open mouth therethrough.

SUMMARY OF THE INVENTION

In accordance with the invention, a bite block for facilitating a dentist's access to a patient's mouth comprises an open-ended, U-shaped body. A pair of arms extend from a bight portion of the U-shaped body, and thereby define a void that is bounded in part by the arms and the bight portion. The bight portion includes one or more strengthening ribs extending between the arms. Thus, when the bite block is positioned between upper and lower teeth of the patient's mouth, the dentist will have access to the patient's mouth through the void.

Preferably, the arms include a textured exterior surface which is adapted for aiding traction on the bite block by the upper and lower teeth. In another aspect of the invention, the textured exterior surface and the arms are made from polymer plastic having different durometers, and preferably, the plastic polymer of the textured exterior surface is a softer durometer than the polymer plastic of the arms. In a preferred embodiment, the polymer plastic of the textured exterior surface is santoprene, and the polymer plastic of the arms is polypropylene.

In another aspect of the invention, the textured exterior surface includes a series of serrations. Preferably, the series of serrations is longitudinally flanked by side walls disposed transversely to the serrations so that the upper and lower teeth are restrained on the bite block.

In a further aspect of the invention, the bite block will have strengthening ribs disposed on opposite outer edges of the bight portion.

BRIEF DESCRIPTION OF THE DRAWINGS

The invention will now be described with reference to the drawings in which:

FIG. 1 is a perspective view of a bite block, according to the invention, in position between the lower and upper teeth of a patient's mouth;

FIG. 2 is an end view of the bite block of FIG. 1;

FIG. 3 is a sectional view of the bite block along line 3—3 of FIG. 1; and

DETAILED DESCRIPTION OF THE PREFERRED EMBODIMENTS

Figure 4:
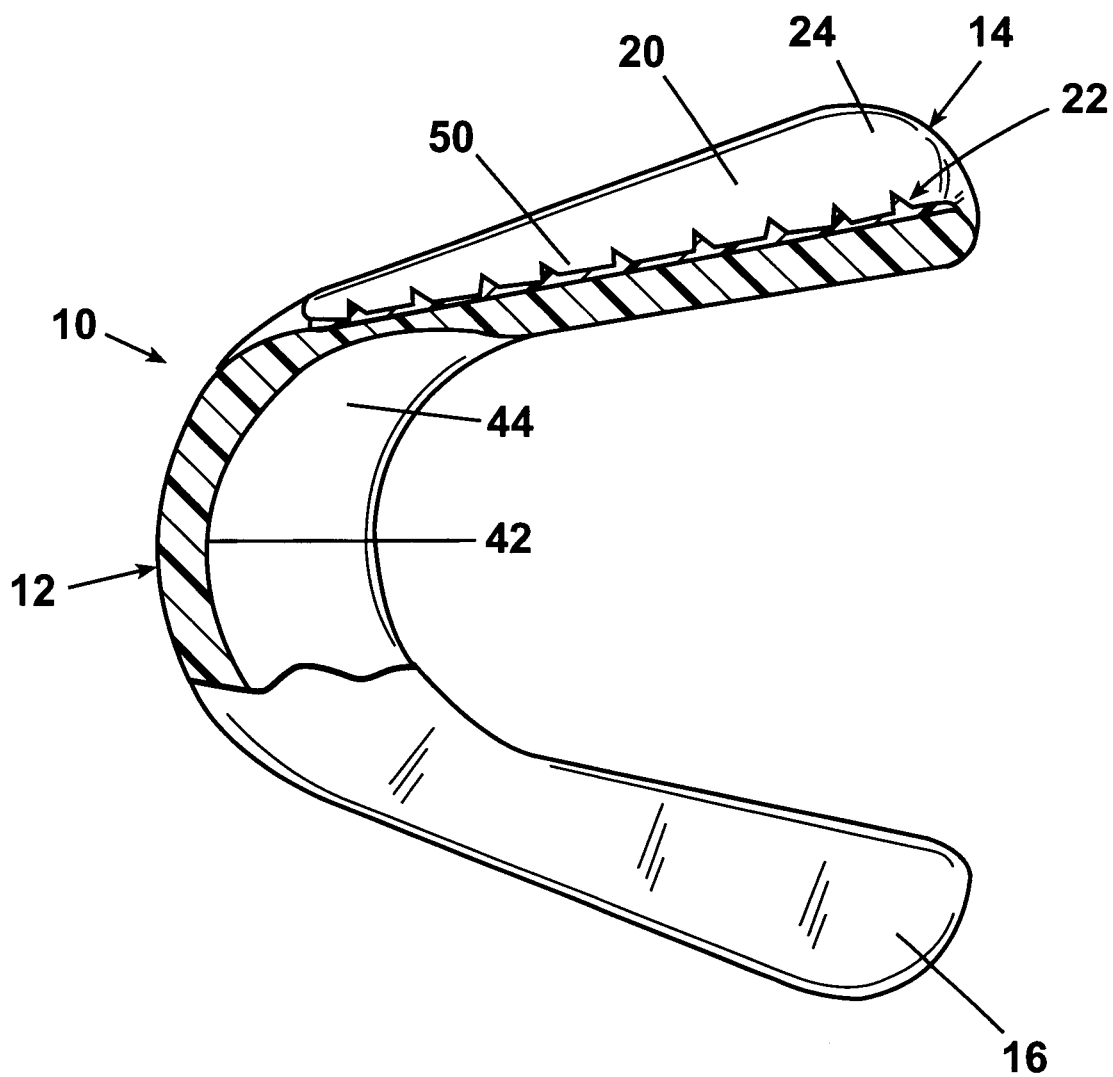
FIG. 4 is a partial sectional view of the bite block along line 4—4 of FIG. 2.

As shown in FIG. 1, a bite block 10 in accordance with the invention is generally U-shaped and includes a bight portion 12 from which extends a pair of arms 14 and 16, thereby partially defining a void 40. The bite block 10 is preferably made from a resilient thermoplastic polymer, such as polypropylene, having a durometer such that there is some flexibility in the bight portion 12, enabling it to act as a spring hinge while maintaining the bite block's unitary structure. The resilient material allows the patient to bite into the block 10 without discomfort and without destroying the block 10 while permitting the block 10 to flex at the bight portion 12.

The U-shape of the block 10 generally conforms to the preferred angle defined by the surfaces of the upper and lower teeth 30 when the mouth 32 is open a sufficient amount to enable adequate working space. Preferably, the distance between free ends of the arms 14, 16 is approximately between 1.125 inches and 1.500 inches, and the distance between the ends of the arms 14, 16 at the bight portion 12 is preferably between 0.250 and 0.750 inches. Of course, the sizes may vary depending on the intended use. For instance, a pediatric bite block would be smaller. Further, the bight portion 12 flexes, allowing arms 14 and 16 to move toward one another to accommodate smaller mouth 32 openings when the block 10 is engaged by the teeth 30.

The outside convex portion of the bite block 10 includes a channel 20 defined by a bottom portion 22 and sidewalls 24. The bottom portion 22 includes a textured exterior surface 50 adapted to better grip the teeth 30 and prevent the block 10 from slipping. Preferably, the textured surface 50 comprises a series of serrations extending between and normal to the sidewalls 24. As shown, each serration has a cross section generally forming a right triangle; other geometric shapes, however, are contemplated including other triangles, such as an isosceles triangle. Further, other surface textures, such as knurling, can be applied to the bottom portion 22 to generate the teeth-gripping surface. Further, the sidewalls 24 prevent the block 10 from slipping or dislodging in a sideways direction when the teeth 30 rest in the channel 20. Moreover, the sidewalls 24 of the channel 20 add stability to the bite block 10 by resisting flexure at the bight portion.

Preferably, the channel 20, and particularly the textured exterior surface 50 of the bottom portion 22, is made of a resilient material, such as santoprene, having a softer durometer than the material comprising the remainder of the block 10. Thus, the block 10 is preferably molded from a pair of polymer plastics such that the bottom portion 22 and the channel 20 are made of the same base material but have different durometers, or are made of different materials that are bonded to one another. To simplify the molding process, a two-step overlay injection molding process is preferred for manufacturing the bite block 10. In one embodiment of the block 10, for example, the block 10 is formed from polypropylene via a first injection molding step. Once the block 10 has hardened, it is trimmed and the channel 20 is injection molded directly onto the block 10 in a second injection molding step. As noted above, the channel 20 is preferably made from santoprene, which will bond securely to the polypropylene block 10 during the second injection molding step without any adhesive. Of course, other materials having similar properties can be used, and the two pieces can be molded separately and bonded together with adhesive. Alternatively, the textured surface 50 can be integrally formed with the block 10 as a single unit out of the base material.

Because the block 10 is substantially U-shaped, its inner or concave portion partially defines a void 40. When the block 10 is inserted in the patient's mouth, the void 40 provides room for the dentist or assistant, or both, to have additional working area within the mouth 32, and further facilitates placement of instruments such as drill (not shown) or a vacuum (not shown) in the mouth 32 of the patient. Moreover, visibility for the dentist or assistant into the mouth 32 is enhanced. The bite block 10 does not interfere with the working area of the dentist as prior mouth props have done.

The bight portion 12 avoids the need for several different sizes of bite blocks, as is common with prior bite block designs. When the bite block 10 is inserted into the patient's mouth 32, the bight portion 12 flexes slightly such that arms 14 and 16 approach one another in the void 40 to accommodate the size of the particular patient's mouth 32. Thus, to facilitate flexing, the block 10 includes a thin flexible portion 42 of the bight portion 12. The thinner portion 42 is flanked by strengthening ribs 44, which are disposed on opposite outer edges of the bight portion 12. The ribs 44 strengthen the bight portion 12, whereby the bight portion 12 provides adequate resistance to biting forces exerted on the arms 14 and 16 by the teeth 30 so that the dentist can continue working even when the patient bites down hard on the block 10. By design, however, the bite block 10 permits the patient to rest the teeth 30 within the channel 20 while the patient's jaw relaxes.

The bite block 10 allows the dentist and assistant access to the patient's mouth 32 from any direction. This design increases the safety of the patient, doctor, and the assistant while preparing or operating within the patient's mouth 32.

Reasonable variation and modification are possible within the spirit of the foregoing specification and drawings without departing from the scope of the invention.

What is claimed is:

1. A bite block for facilitating a dentist's access to a patient's mouth comprising an open-ended, U-shaped body including a pair of arms extending from a bight portion, thereby defining a void that is bounded in part by the arms and the bight portion, the bight portion including strengthening ribs extending between the arms, whereby when the bite block is positioned between upper and lower teeth of the patient's mouth the dentist will have access to the patient's mouth through the void.

2. A bite block according to claim 1 wherein the strengthening ribs are disposed on opposite outer edges of the bight portion.

3. A bite block according to claim 1 wherein the arms include a textured exterior surface adapted for aiding traction on the bite block by the upper and lower teeth.

4. A bite block according to claim 3 wherein the textured exterior surface and the arms are made from polymer plastics having different durometers.

5. A bite block according to claim 4 wherein the plastic polymer of the textured exterior surface is a softer durometer than the polymer plastic of the arms.

6. A bite block according to claim 5 wherein the polymer plastic of the textured exterior surface is santoprene, and the polymer plastic of the arms is polypropylene.

7. A bite block according to claim 5 wherein the textured exterior surface includes a series of serrations.

8. A bite block according to claim 7 wherein the series of serrations is longitudinally flanked by side walls disposed transversely to the series of serrations, whereby the upper and lower teeth are restrained on the bite block.

9. A bite block according to claim 3 wherein the textured exterior surface is longitudinally flanked by side walls, whereby the upper and lower teeth are confined to the textured exterior surface on the bite block.

10. A bite block according to claim 3 wherein the textured exterior surface includes a series of serrations.

11. A bite block according to claim 10 wherein the series of serrations is longitudinally flanked by side walls disposed transversely to the series of serrations, whereby the upper and lower teeth are restrained on the bite block.

12. A bite block for facilitating a dentist's access to a patient's mouth comprising an open-ended U-shaped body including a pair of arms extending from a bite portion, thereby defining a void that is bounded in part by the arms in the bite portion, the bite portion including at least one strengthening rib extending between the arms, whereby when the bite block is positioned between upper and lower teeth in the patient's mouth, the dentist will have access to the patient's mouth through the void.

13. A bite block according to claim 12 wherein the arms include a textured exterior surface adapted for aiding traction on the bite block by the upper and lower teeth.

14. A bite block according to claim 13 wherein the textured exterior surface and the arms are made from polymer plastics having different durometers.

15. A bite block according to claim 14 therein the plastic polymer of the textured exterior surface is a softer durometer than the polymer plastic of the arms.

16. A bite block according to claim 15, wherein the polymer plastic of the textured exterior surface is santoprene, and the polymer plastic of the arms is polypropylene.

17. A bite block according to claim 13 wherein the textured exterior surface includes a series of serrations.

18. A bite block according to claim 17 wherein the series of serrations is longitudinally flanked by side walls disposed transversely to the series of serrations, whereby the upper and lower teeth are restrained on the bite block.

* * * * *

UNITED STATES PATENT AND TRADEMARK OFFICE
CERTIFICATE OF CORRECTION

PATENT NO. : 6,241,521 B1
DATED : June 5, 2001
INVENTOR(S) : John E. Garrison

It is certified that error appears in the above-identified patent and that said Letters Patent is hereby corrected as shown below:

<u>Column 5, claim 15,</u>
Line 10, "therein" should be -- wherein --.

Signed and Sealed this

Nineteenth Day of February, 2002

*Attest:*

JAMES E. ROGAN
*Attesting Officer*     *Director of the United States Patent and Trademark Office*